(12) United States Patent
Baynham

(10) Patent No.: US 9,445,920 B2
(45) Date of Patent: Sep. 20, 2016

(54) SPINAL IMPLANT DEVICE

(71) Applicant: Atlas Spine, Inc., Jupiter, FL (US)

(72) Inventor: Matthew G. Baynham, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 0 days.

(21) Appl. No.: 14/294,889

(22) Filed: Jun. 3, 2014

(65) Prior Publication Data

US 2015/0342748 A1 Dec. 3, 2015

(51) Int. Cl.
*A61F 2/44* (2006.01)

(52) U.S. Cl.
CPC ........ *A61F 2/447* (2013.01); *A61F 2002/4475* (2013.01)

(58) Field of Classification Search
CPC ................. A61F 2/442; A61F 2/4425; A61F 2002/4435
USPC ..................... 623/17.11–17.16; 606/246–249
See application file for complete search history.

(56) References Cited

U.S. PATENT DOCUMENTS

| | | | |
|---|---|---|---|
| 6,176,882 B1 | 1/2001 | Biedermann et al. | |
| 7,850,733 B2 | 12/2010 | Baynham et al. | |
| 8,062,375 B2 | 11/2011 | Glerum et al. | |
| 8,105,382 B2 | 1/2012 | Olmos et al. | |
| 8,273,179 B2 | 9/2012 | Kim et al. | |
| 8,361,152 B2 | 1/2013 | McCormack et al. | |
| 8,382,842 B2 | 2/2013 | Greenhalgh et al. | |
| 8,398,713 B2 | 3/2013 | Weiman | |
| 8,435,298 B2 | 5/2013 | Weiman | |
| 8,491,659 B2 | 7/2013 | Weiman | |
| 8,518,120 B2 | 8/2013 | Glerum et al. | |
| 8,556,979 B2 | 10/2013 | Glerum et al. | |
| 8,568,481 B2 | 10/2013 | Olmos et al. | |
| 8,632,595 B2 | 1/2014 | Weiman | |
| 8,685,098 B2 | 4/2014 | Glerum et al. | |
| 8,709,086 B2 | 4/2014 | Glerum | |
| 8,888,853 B2 | 11/2014 | Glerum et al. | |
| 8,888,854 B2 | 11/2014 | Glerum et al. | |
| 9,034,045 B2 | 5/2015 | Davenport et al. | |
| 9,149,367 B2 | 10/2015 | Davenport et al. | |
| 2006/0122701 A1* | 6/2006 | Kiester ................... | A61F 2/447 623/17.11 |
| 2008/0140207 A1 | 6/2008 | Olmos et al. | |
| 2009/0312763 A1 | 12/2009 | McCormack et al. | |
| 2010/0292796 A1* | 11/2010 | Greenhalgh ....... | A61B 17/8858 623/17.11 |
| 2011/0093074 A1* | 4/2011 | Glerum et al. ............ | 623/17.16 |
| 2014/0180421 A1 | 6/2014 | Glerum et al. | |

* cited by examiner

*Primary Examiner* — Ellen C Hammond
*Assistant Examiner* — Christina Negrellirodrigue
(74) *Attorney, Agent, or Firm* — McHale & Slavin, P.A.

(57) ABSTRACT

A spinal fusion device that is expandable. The device features a top and bottom surface for engaging adjacent vertebrae, a hollow center for stacking of bone or bone growth material, and a slidable mechanism with grooves for expanding or unexpanding the device.

16 Claims, 4 Drawing Sheets

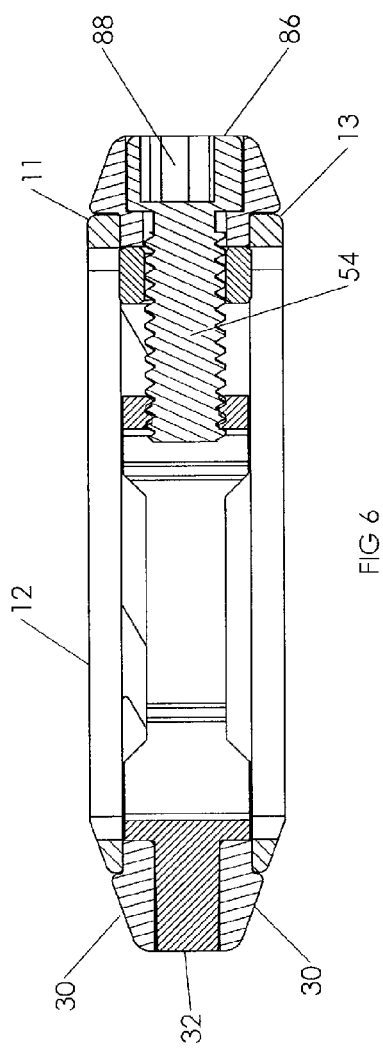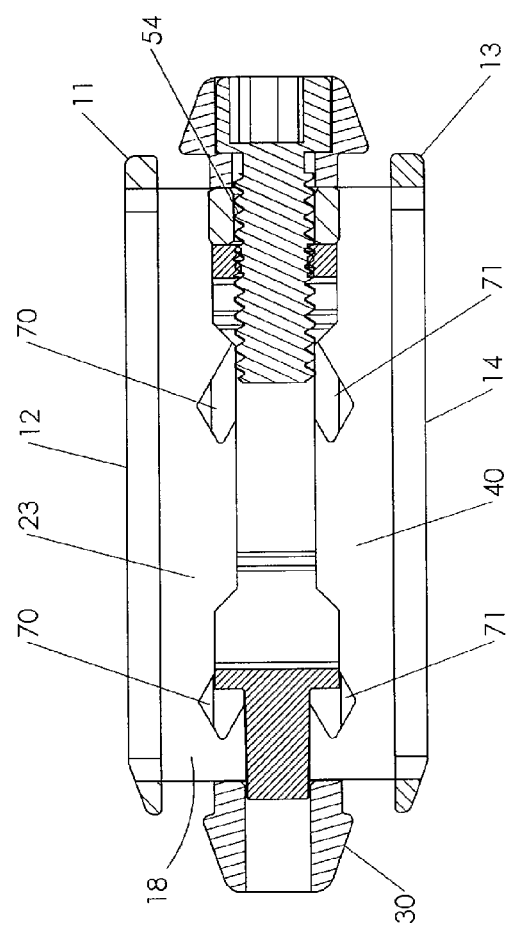

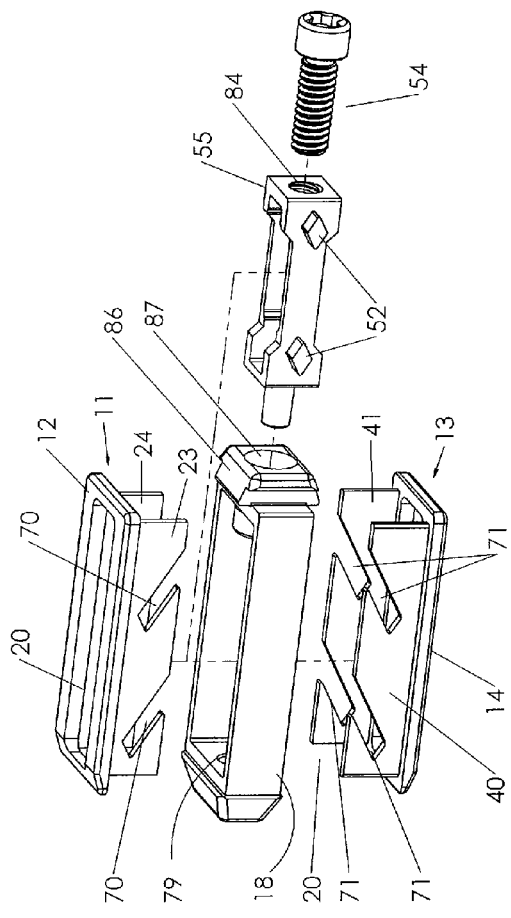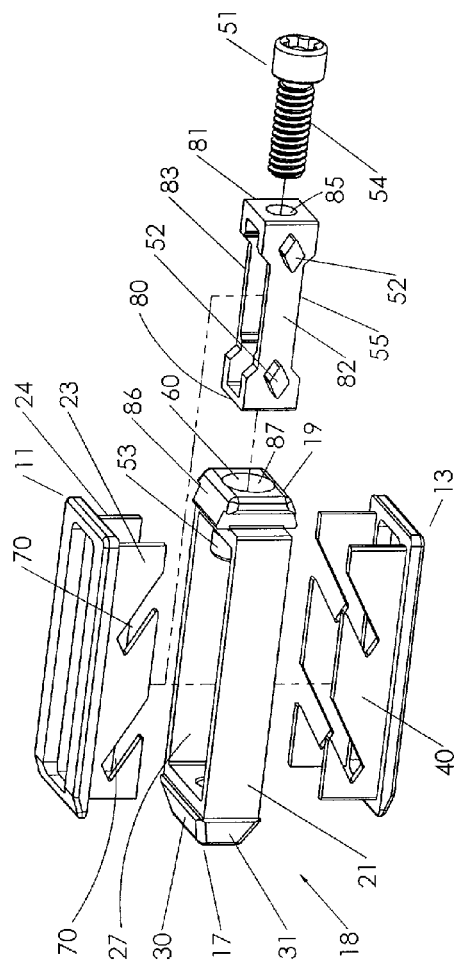

SPINAL IMPLANT DEVICE

FIELD OF THE INVENTION

Embodiments of the invention relate to the field of orthopedic surgery, and more particularly, to implants to be placed between vertebrae in the spine.

BACKGROUND

Spinal stabilization is one approach to alleviating chronic back pain caused by disabled disk material or excessive movement of individual vertebrae. Conventional stabilization techniques include fusing two or more vertebrae together to circumvent or immobilize the area of excessive movement. Normally, the vertebral disk material which separates the vertebrae is removed and bone graft material is inserted in the space for interbody fusion. In addition to, or in place of, the bone graft material, a spinal implant may be inserted in the intervertebral space.

The conventional surgical approach for stabilization has been posteriorly for ease of access to the spine and to avoid interfering with internal organs and tissues. Usually the implant site is prepared to maintain natural lordosis and to accept, a certain sized implant within certain pressure limits. This requires considerable time and skill by the surgeon.

DESCRIPTION OF THE PRIOR ART

U.S. Pat. No. 8,556,979, issued Oct. 15, 2013, describes an expandable fusion device capable of being installed inside an intervertebral disc space to maintain normal disc spacing and restore spinal stability. The fusion device includes a body portion, a first end plate, and a second end plate; both of these end plates can be moved in a direction away from the body portion or towards the body portion into an unexpanded configuration.

SUMMARY OF THE INVENTION

Embodiments of the invention are directed to an expandable spinal fusion device comprising upper and lower sections with depending sidewalls forming a cube-like or rectangular structure with a hollow center. The upper and lower sections comprise a top and a bottom surface, respectively, for engaging adjacent vertebrae, a slidable mechanism for expanding or compacting the device, and a hollow center allowing for packing with bone graft or similar bone growth inducing material. The slidable mechanism comprises slots or grooves on each of the sidewalls depending from the top and bottom surfaces, and a distractor. The distractor comprises a rod, a body and an actuator for enabling distraction. The rod can be telescopic or a jack screw type rod. The distractor comprises a body with protruding members, rollers or pins, for engaging the grooves which are positioned in the exact location directly opposite from each other. When the distractor is actuated, the body slides upwards, downwards or sideways depending on the groove geometry.

The device is inserted between the adjacent vertebrae and expanded or increased in height to engage the opposing surfaces of the adjacent vertebra. The adjacent vertebrae are forced apart as the height of the implant increases. The spinal fusion device may be used unilaterally or bilaterally.

Accordingly, it is an objective of the instant invention to teach a posterior surgical approach for placement of an adjustable spinal implant for interbody fusion, allowing the implant to be inserted through a small incision and increased in size in situ.

It is another objective of the instant invention to teach a spinal implant which allows the surgeon to provide for lordosis intraoperatively and to distract through the implant.

It is yet another objective of the instant invention to teach an implant facilitating interbody fusion through bone graft or an ingrowth type implant.

Although embodiments are directed to posterior surgical approaches and to provide for lordosis intraoperatively, it is to be understood that the invention may be employed in cervical and thoracic spinal procedures as well as from any direction, that is, anterior, posterior and lateral.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

FIG. 6 is a cross sectional of FIG. 2;
FIG. 7 is a cross section of FIG. 4;
FIG. 8 is an exploded view of the implant with an alignment tube;
FIG. 9 is an exploded view of the implant without an alignment tube.

DETAILED DESCRIPTION

Figure 1:
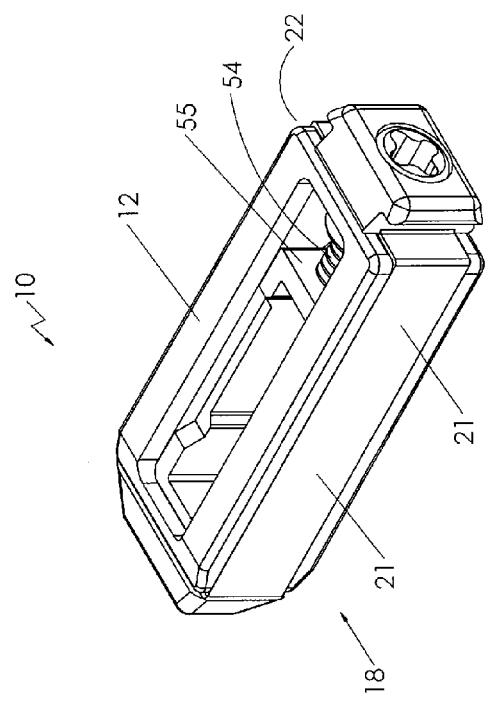
FIG. 1 is a perspective view of the spinal implant in a contracted position.
Figure 2:
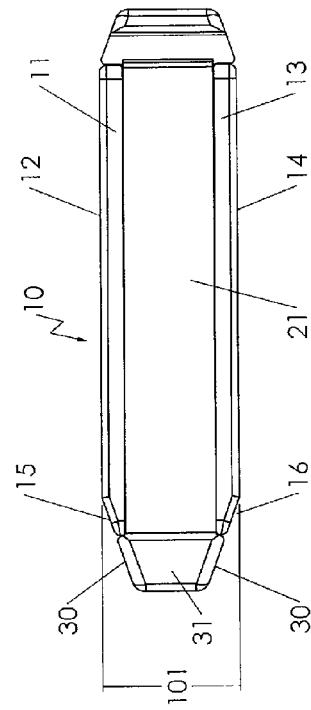
FIG. 2 is a side view of FIG. 1.
Figure 3:
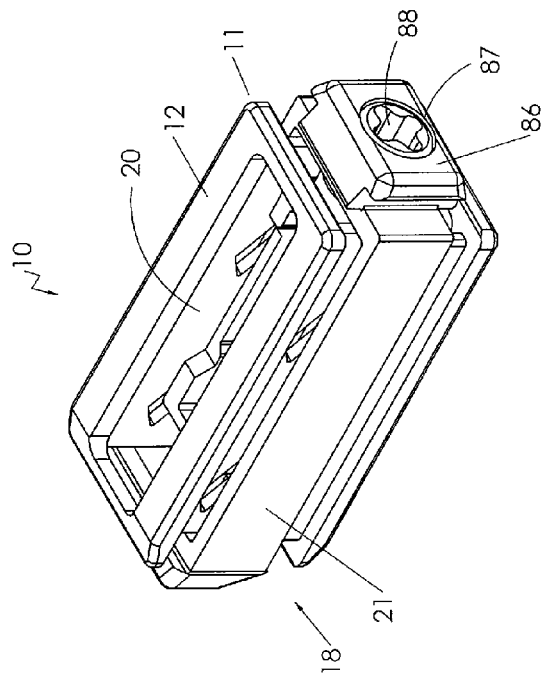
FIG. 3 is a perspective view of the spinal implant in an expanded position.
Figure 4:
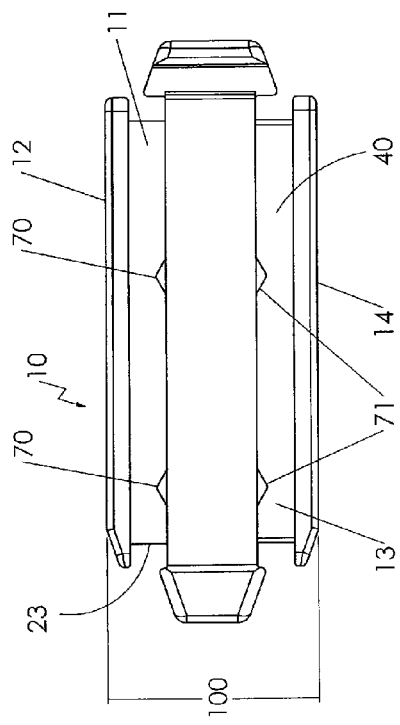
FIG. 4 is a side view of FIG. 3.
Figure 5:
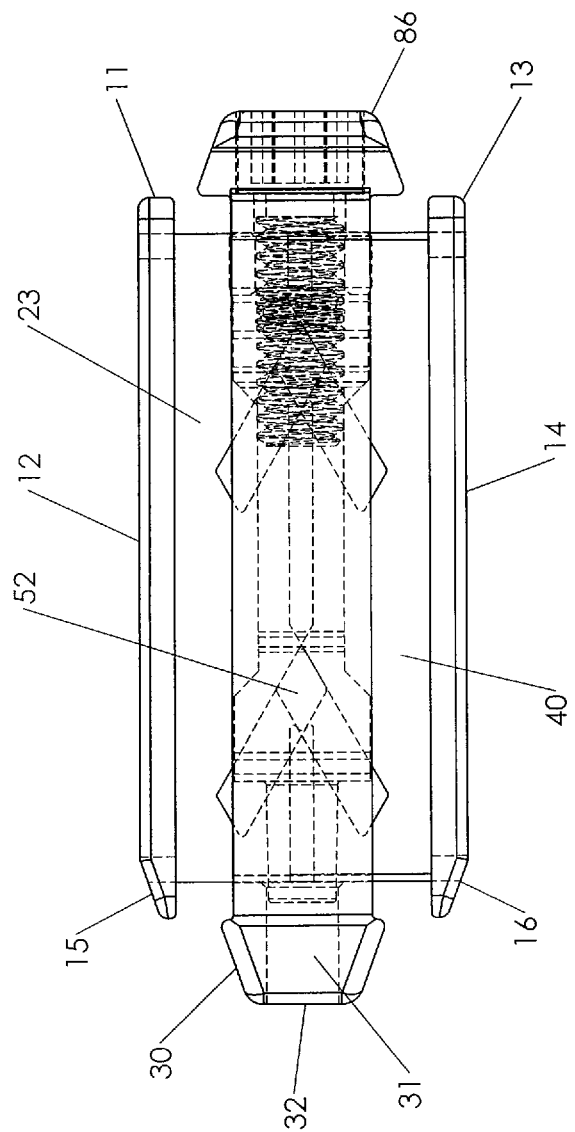
FIG. 5 is a cross sectional overlay of FIG. 4.

The following description of the preferred embodiments is merely exemplary in nature and is in no way intended to limit the invention, its application or uses.

It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Embodiments of the invention may be practiced without the theoretical aspects presented. Moreover, the theoretical aspects are presented with the understanding that Applicants do not seek to be bound by the theory presented.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Expandable Spinal Fusion Device(s)

A spinal fusion is typically employed to eliminate pain caused by the motion of degenerated disk material. Upon successful fusion, a fusion device becomes permanently fixed within the intervertebral disc space.

Referring now to the Figures, the spinal fusion device 10 is inserted into the intervertebral space in the insertion mode to replace damaged, missing or excised disk material. In an exemplary embodiment, the device 10 comprises an upper section 11, a top surface 12, a lower section 13, a bottom surface 14, a body portion 18 and a distractor 55. The device may be made of conventional materials used for surgical implants, such as stainless steel and its many different alloys, titanium, titanium alloys, metallic alloys, polymeric materials, plastics, plastic composites, ceramic and any other metal or material with the requisite strength and biologically inert properties.

In an exemplary embodiment, the upper section 11 of the device 10 comprises a top surface 12 for engaging the end plate of a vertebra and the lower section 13 comprises a bottom surface 14 for engaging the end plate of adjacent vertebra. The top surface 12 and bottom surface 14 are planar to provide large contact areas with each vertebra. In an exemplary embodiment, the top and bottom surfaces 12 and 14 each end at one end with a sloping or angled edge 15, 16 running the width of the top 12 and bottom 14 surfaces, respectively. In an exemplary embodiment, the top surface ends with an edge 15 sloped towards the bottom surface, and the bottom surface comprises an edge 16 sloped towards the top surface. In other embodiments, only the top surface has a sloped edge. In another embodiment, only the bottom surface has a sloped edge. In yet other embodiments, the top and bottom surfaces lack a sloped edge.

The device 10 is hollow 20, allowing for insertion of bone graft, bone graft material, scaffolds or any tissue or cellular material. In an exemplary embodiment, bone graft or similar bone growth inducing material can be introduced around and within the fusion device to further promote and facilitate bone fusion. The fusion device is hollow in the center, further providing a space for packing with bone graft or similar bone growth inducing material. Such bone graft or bone growth inducing material can be packed, prior to, subsequent to, or during implantation of the fusion device.

The device 10 has two extreme positions and is adjustable infinitely between these positions. The expanded position 100 is the sum of the height of the upper section 11 and the lower section 13. The compact position 101 is the height of the sides 21 or 22 of the body portion and the sum of the thickness of the top surface 12 and bottom surface 14. The top surface 12 and the bottom surface 14 contact the body portion 18 when the device is in a compact or unexpanded position with the upper section side walls 23 being able to slidably fit into the hollow area. It is to be understood that the placing of the side walls of the upper and lower sections is interchangeable, in that the sidewalls of the lower section can be placed at a distance further apart than the side walls of the upper section. In this embodiment, the upper section sidewalls slide down the inner side walls of the lower section sidewalls. Conversely, the upper section side walls are placed at a wider distance than the lower section sidewalls so that the upper section sidewalls slide over the lower section side walls during the extension or when the device is in a compacted position. In another embodiment, the upper and lower section sidewalls are placed equidistant from each other so that the sidewalls rest upon each other when the device is in the unexpanded or compact position. The device can be rotated along the longitudinal axis 180 degrees so that the upper section becomes the lower section and vice versa.

The upper section 11 comprises a top surface 12 with a large aperture 20 to facilitate bone ingrowth after implantation, and opposing depending sidewalls 23 and 24 projecting from the top surface 12 and positioned parallel to each other. The depending side walls 23, 24 terminate in a flat plane and each side wall possesses at least one slot or groove 70 for engaging a protruding member, rollers or pins 52 of the distractor body 55; the protruding member dimensioned to slidably fit in the slots or grooves 70. The angle of the slot or groove relative to a 90° angle to the horizontal plane can vary so that the maximum expanded position can be increased or decreased. For example, if the groove is vertical at a 90° angle to the horizontal plane, the maximum expanded position is greater than if the slot or groove is at a 45° angle to the horizontal plane. However, it is to be understood that a slot or groove having, for example, a 45° angle to the horizontal plane would not only expand the device vertically, but also horizontally. The slot or groove 70 engages the protruding member 52 of the distractor 55 to guide the relative movement of the sections, maintaining the distractor and the depending sidewalls in alignment.

The bottom surface 14 of the lower section 13 has a large aperture 20 to facilitate bone ingrowth after implantation. The lower section 13 comprises opposing upstanding sidewalls 40, 41 projecting from the bottom surface 14 and positioned parallel to each other. The distance between the opposing sidewalls 40, 41 is dimensioned to be less than the distance between the opposing sidewalls 23 and 24 of the upper section 11 so that the upper and lower sections can slidably move between the expanded and compact positions of the device. The depending side walls 40 and 41 terminate in a flat plane, and each side wall possesses at least one slot or groove 71 for engaging a protruding member 52 of the distractor 55, dimensioned to slidably fit in the slots or grooves 71. The protruding member can be any type, size or shape, for example, rollers, pins, as long as these protruding members can be engaged by the slots or grooves 71. The angle of the slots or grooves 71 of the lower depending side walls 40 and 41 and the angle of the slots or grooves 70 of the upper depending side walls 23 and 24 is greater than 0° and up to 180° relative to each other. The slots or grooves 70, 71 engage the protruding members, rollers or pins 52 of the distractor 55 to guide the relative movement of the sections, maintaining the distractor and the depending sidewalls in alignment. The slots or grooves 70, 71 on each opposing sidewall are diametrically opposed on the opposite side walls.

The depending sidewalls of the upper and lower sections and the slot or groove of each sidewall are smooth to provide ease in the relative sliding contact between the sidewalls and between the protruding members 52 of the distractor. In alternative embodiments, the slots or grooves may comprise jagged steps which are positioned to provide a lock-step expansion when the device height is adjusted.

In an exemplary embodiment, the device 10 comprises a body portion 18. In an exemplary embodiment, the body portion 18 has a first end 17, a second end 19, a first side portion 26 connecting the first end 17 and the second end 19 and a second side portion 27 connecting the first end 17 and the second end 19. The first end 17 of the fusion device 10 includes at least one angled surface, a grooved end and a flat end or planar end plate. In preferred embodiments, the first end 17 comprises multiple angled surfaces. In an exemplary embodiment, there are at least two opposing angled surfaces 30, 31 forming a generally wedge-shape. In other preferred embodiments, there are at least two opposing angled surfaces 30, 31 and a flat end or planar end plate 32 wherein the angled surfaces do not meet but culminate at the flat end 32 at a first end, forming a generally wedge shape; and at the opposing end, the angled surfaces culminate to form a receptacle for receiving the sloped edges of the top and bottom surfaces when the device is in a compacted or unexpanded form. In an exemplary embodiment, the top edge 15 and the bottom edge 16 are angled so as to run parallel with the angled surfaces 30 of the first end 17.

The second end 19 includes an opening 60 which may include threading. The opening 60 is dimensioned to fit a distractor 55. In an exemplary embodiment, the distractor 55 comprises an actuation member 51, a rod 54 and a distractor body 55. The actuation member 51 is located on the outer surface 52 of the second end 19, and a member 53 of the second end 19 aligns the rod 54 with the distractor body 55. The rod 54, which extends into the hollow area of the distractor body 55, may be threaded or telescopic for slidably moving the distractor body 55 within the hollow center of the device 10. Although the term "rod" is used, it is merely descriptive and encompasses any shape or form as long as it can move the body of the distractor. In an exemplary embodiment, the distractor body 55 is dimensioned to fit in the hollow center of the device and to provide a large volume for the placing of bone graft, bone graft inducing material, scaffolds or any tissue or cellular material. In an exemplary embodiment, the rod 54 is attached to the distractor body 55. The distractor body 55 comprises a first end 80, a second end 81, a first side portion 82 connecting the first end 80 to the second end 81, and a second side portion 83 connecting the first end 80 to the second end 81. The first side portion 82 and the second side portion 83 each comprise at least one, preferably two protruding members, rollers or pins 52 which are dimensioned to slidably fit into the grooves or slots 70, 71 in the sidewalls of the upper and lower sections. The first end 80, in exemplary embodiments is a planar surface. In some embodiments, an alignment tube 84 is attached at the center of the planar surface of the first end 80. The alignment tube 84 may be hollow and threaded, or may be hollow and smooth, and dimensioned for insertion into support aperture 79. In preferred embodiments, the rod 54 is a jack screw for engagement of a threaded bore 85 at the second end 81 of the distractor body 55. A bracket 86 is attached to the second end 19 of the body portion 18. In an exemplary embodiment, the bracket 86 comprises a bore 87 which has a larger countersunk bore 88 for receiving the rod 54. The bore 87 and countersunk bore 88 are aligned with the bore 85 of the distractor body 55. As illustrated in FIG. 9, the alignment tube can be removed and still provide stability to the distractor.

The distance between the top surface 12 and the bottom surface 14 is adjustable by moving the upper section 11 relative to the lower section 13. The protruding members 52 of the distractor slide downwards when the distractor is actuated and the distance between the upper and lower section decreases. Conversely, the protruding members 52 of the distractor slide upwards when the distractor is actuated and the distance between the upper 11 and lower section 13 increases. The distractor can be a telescopic mechanism whereby the distractor comprises a member, for example, a telescopic rod, for moving the distractor body 55 by a sliding mechanism and, optionally, a locking mechanism to lock the distractor at a desired position. The distractor is not limited to a sliding mechanism, but can utilize any mechanism as long as the distractor can cause the distractor body 55 to move.

The device is inserted into the disk space between adjacent vertebrae with the top surface in contact with the end plate of one vertebra and the bottom surface in contact with the end plate of the adjacent vertebra. When the surgeon actuates the distractor, the rod 54 is extended into the cavity, pushing the distractor body 55 and the protruding members 52 to slide along the slots or grooves 70, 71 thereby changing the distance between the top and bottom surfaces 12, 14 as the sidewalls move apart, thereby expanding the device 10. When the actuator is actuated in the opposite direction, the rod member 54 retracts, pulling the distractor body 55 towards the end of the outer wall to which the distractor 55 is fastened. The extending of the rod member 54 can be accomplished by a variety of means, including a pushing or pulling mechanism or a rotating mechanism utilizing a screw and thread means. The telescopic rod, in this embodiment, comprises one or more rods of equal and/or varying lengths, each rod having a circumference slightly smaller than the previous rod so that when the actuator is actuated the rods can extend beyond the length of the first rod or retract into each other.

The invention has been described in detail with reference to preferred embodiments thereof. However, it will be appreciated that those skilled in the art, upon consideration of this disclosure, may make modifications and improvements within the spirit and scope of the invention. The following non-limiting examples are illustrative of the invention.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention.

What is claimed is:

1. A spinal fusion device for implanting or placing between adjacent vertebrae comprising:
    a hollow body having an upper section with a top surface for contacting one vertebra and a lower section having a bottom surface for contacting an adjacent vertebra, said top surface and said bottom surface having a means for engaging the vertebra, each section having depending sidewalls, a top sidewall being slidably mounted over a bottom sidewall, each sidewall having at least one slot;
    a hollow body section, said body section having a first end comprising a multitude of angled surfaces, a grooved end and a flat end, wherein the angled surfaces culminate at a flat end or planar end plate at a first end, and at the opposing end, the angled surfaces culminate for receiving a sloped edge of the top and bottom surfaces when the device is in a unexpanded form and a second end comprising an opening for disposing of a distractor; and, a distractor having a body with a bore with at least one protruding member for engaging at least one said slot on each said sidewall, and a jack screw threaded into the bore whereby the distractor moves relative to the rotation of the jack screw.

2. The spinal fusion device of claim 1, wherein the distractor comprises:

an actuator at one end of an elongated member disposed through the opening of the second end of the hollow body section;

whereby the distance between the top and bottom surfaces is adjustable as the protruding members of the distractor body move within the slots thereby moving the upper section relative to the lower section.

3. The spinal fusion device of claim 2, wherein the elongated member comprises threading for slidably moving the distractor body.

4. The spinal fusion device of claim 1, wherein the opening on the second end of the body section of the device further comprises threads for engaging a rod member of the distractor and is aligned with an opening in the distractor body for receiving the elongated member and to move the distractor body relative to the depending sidewalls as the actuator is threaded into the opening in the second end of the body section of the device.

5. The spinal fusion device of claim 1, wherein the slot for engaging the protruding members of the distractor body is dimensioned to slidably fit, whereby the distance between the bottom surface and the top surface is adjustable by moving the upper section relative to the lower section.

6. The spinal fusion device of claim 5, wherein the protruding members of the distractor body slidably move in the slots or grooves in a first direction when the distractor is actuated and the distance between the upper and lower section decreases, or the protruding members of the distractor body move in the slots in a second or opposite direction to the first direction when the distractor is actuated and the distance between the upper and lower section increases.

7. The spinal fusion device of claim 1, wherein the sloped edge depending from the top surface is angled downwards toward the bottom surface and the sloped edge depending from the bottom surface angles upwards towards the top surface.

8. The spinal fusion device of claim 1, wherein the hollow body is dimensioned to fit bone or bone graft material.

9. A spinal fusion device for adjusting the space between vertebrae comprising: a hollow body having an upper section with a top surface for contacting one vertebra and a lower section having a bottom surface for contacting an adjacent vertebra, said top surface and said bottom surface having a means for engaging the vertebra, each section having depending sidewalls, the top sidewall being slidably mounted over the bottom sidewall, each sidewall having a slot or groove for engaging a distractor, the distractor comprising a bore, a jack screw in the bore threaded into a rod member whereby the distractor moves relative to the bottom surface as the jack screw is threaded into the distractor body, said sidewalls surrounded by a body section comprising a first end having angled surfaces and a second end having an opening for disposing of the distractor.

10. The spinal fusion device of claim 9, wherein rod member is attached to the actuator for adjusting the distractor, whereby the distance between the top and bottom surfaces is adjustable by moving the upper section relative to the lower section, the upper and lower section depending side walls comprising slots for engaging protruding members of the distractor body, wherein the protruding members are dimensioned to fit into the sidewall slots for slidably moving the top and bottom surfaces.

11. The spinal fusion device of claim 9, wherein the top and bottom surfaces further comprise a sloped edge wherein the sloped edges are angled towards each other.

12. The spinal fusion device of claim 9, wherein the body section comprises a first end, a second end, a first side portion and a second side portion connecting the first and second ends.

13. The spinal fusion device of claim 12, wherein the first end comprises at least one angled surface and an end plate, and the second end comprises a bracket having a bore for receiving the distractor.

14. The spinal fusion device of claim 12, wherein the first end comprises at least two first angled surfaces, at least two second angled surfaces and a flat end plate, at which the two first and second angled surfaces culminate.

15. The spinal fusion device of claim 9, wherein the upper and lower sections further comprise a means for engaging a vertebra, the engaging means comprising a bracket.

16. The spinal fusion device of claim 9, wherein the hollow body is dimensioned to fit bone or bone graft material.

\* \* \* \* \*